United States Patent [19]

Thun

[11] 4,052,994
[45] Oct. 11, 1977

[54] DENTAL FLOSS APPLICATOR

[76] Inventor: Floyd A. Thun, 645 Adelaide Drive, Santa Monica, Calif. 90402

[21] Appl. No.: 676,049

[22] Filed: Apr. 12, 1976

[51] Int. Cl.[2] ............................................. A61C 15/00
[52] U.S. Cl. ................................................. 132/92 R
[58] Field of Search ...................... 133/92 A, 92 R, 91

[56] References Cited

U.S. PATENT DOCUMENTS

| 754,841 | 3/1904 | Bessonet | 132/92 A |
| 1,468,942 | 9/1923 | Gamble | 132/92 R |
| 2,197,345 | 4/1940 | Meyer | 132/92 A |
| 3,949,769 | 4/1976 | Minka | 132/91 |

Primary Examiner—G.E. McNeill
Attorney, Agent, or Firm—Clarence A. O'Brien; Harvey B. Jacobson

[57] ABSTRACT

A dental floss applicator has a receptacle for receiving a spool of dental floss therein and rewind and tension means associated with the receptacle and receptacle closure top for maintaining the dental floss under a certain degree of tension. A projecting holder from the receptacle top has two spaced tines extending therefrom for stretching a piece of clean dental floss therebetween. The structure is so designed that additional tension may be applied to the stretched piece of dental floss by the user's index finger while holding the applicator in one hand in an easy and comfortable manner.

5 Claims, 4 Drawing Figures

DENTAL FLOSS APPLICATOR

BACKGROUND OF THE INVENTION

1. Field of the Invention

This invention relates generally to dental floss applicators having a receptacle for holding a clean spool of dental floss together with spaced apart projections for stretching a clean usable piece of dental floss thereacross and additional means for maintaining tension thereon.

2. Description of the Prior Art

A common problem with known dental floss holders and the like is that they fail to provide sufficient tension upon the dental floss being used therewith in order to properly clean a user's teeth and gums. It is very desirable that an easy means for varying the amount of tension be provided in order to make it handy and convenient for the user of the device to vary same.

Another problem with known prior art devices is that they are inconvenient and awkward to use. Furthermore, many of these devices fail to provide rewind mechanism in order to take up excess slack if such should occur. With devices not providing such a rewind structure, the excess dental floss must be cut off and is thus obviously wasted. This is both expensive, annoying, and inconvenient.

Another problem with known prior art devices is that they fail to permit use of the dental floss spool just as it comes from the manufacturer and is sold by the retail outlet.

Known prior art patents which may be pertinent to this invention are as follows:

U.S. Pat. No. 1,158,890 - Nov. 2, 1915 — Bowling
U.S. Pat. No. 1,438,939 - Dec. 19, 1922 — Ball
U.S. Pat. No. 2,052,520 - Aug. 25, 1936 — Sonnenberg
U.S. Pat. No. 3,759,273 - Sep. 18, 1973 — Knaus
3,858,594 - Jan. 7, 1975 — Ensminger.

None of these known prior art devices offers the new and unique features of the invention disclosed herein.

SUMMARY OF THE INVENTION

An object of the present invention is to provide an improved dental floss applicator device which is easy to use and more efficient in use than known devices.

Another object of the present invention is to provide a dental floss applicator having two methods of tensioning dental floss being used therewith. One structure is used to tension the clean portion of dental floss for direct contact with a user's teeth and gums, while the other tensioning means is for the purpose of reducing slack in the feed-in portion of the dental floss.

A further object of this invention is to provide a dental floss applicator having rewind features, usable dental floss stretching and holding structure, and easily operable tensioning means associated therewith for direct engagement by a user's hand and fingers.

A still further object of this invention is to provide a dental floss applicator which will receive spools of dental floss in the same manner that they are sold and distributed by retail outlets.

The dental floss applicator of this invention has a number of new and unique features. One of these is the top closure for a dental floss spool containing receptacle which has quick attach means associated therewith for quickly attaching and detaching the receptacle thereto. In addition, tensioning means and rewind means are provided for rewinding and taking up any excess slack produced from the dental floss spool itself. Another feature is the provision of extending or projecting holding fingers which define usable space therebetween for stretching a short length of dental floss and holding same therebetween. The arrangement of these projecting fingers in relation to the closure top itself is such that a user's index finger may be readily manipulated in order to apply a proper amount of tension to the stretched piece of dental floss. The entire dispenser or applicator structure is arranged so that it fits a user's hand in a comfortable and easily used manner.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
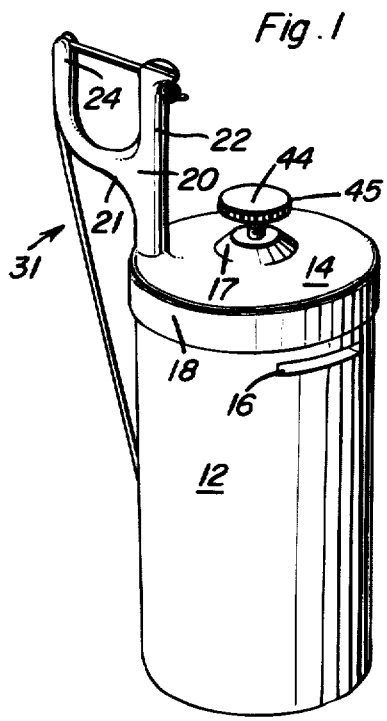
FIG. 1 is a perspective view of the dental floss applicator of this invention.

Referring to FIG. 1 of the drawings, reference numeral 10 indicates in general the dental floss applicator of this invention. A receptacle 12 is provided for receiving the spool of dental floss therein. Looking at FIG. 2 of the drawings, an aperture 13 is spaced approximately midway along the cylindrical wall of the receptacle 12 for receiving and passing therethrough the length of dental floss prior to use thereof. Three or four knobs or projections 15 are provided along the outer edge of the open end of the container or receptacle 12. These projections 15 are for the purpose of engaging with shallow thread-like grooves 15' formed within the inside of the top cover 14. The top cover 14 has a depending cylindrical flange 18 with said flange having the shallow grooves 15' provided therein.

The container top 14 has a conical projection 17 at the center with an appropriate aperture extending through the top center thereof. Along one circumferential edge of the container top 14 is a projecting dental floss holder structure 20. This structure 20 has two members 22 and 24 extending therefrom to form a generally U-shaped dental floss support. The member 22 extends directly in line with the main support portion of the support 20 while the other member 24 is spaced outwardly thereof. A curved recess portion 21 is formed thereby. The space between the two projecting members 22 and 24 is normally one-half inch, but also may be made in a slightly larger spacing of five-eighths of an inch. These two spacings have been found to be most practical. In most instances, these two sizes will be the standard sizes as this device is produced for major market distribution. The outer end of the projection member 24 has a notch 23 provided therein and likewise the member 22 has a slightly larger notch portion 25.

Figure 2:
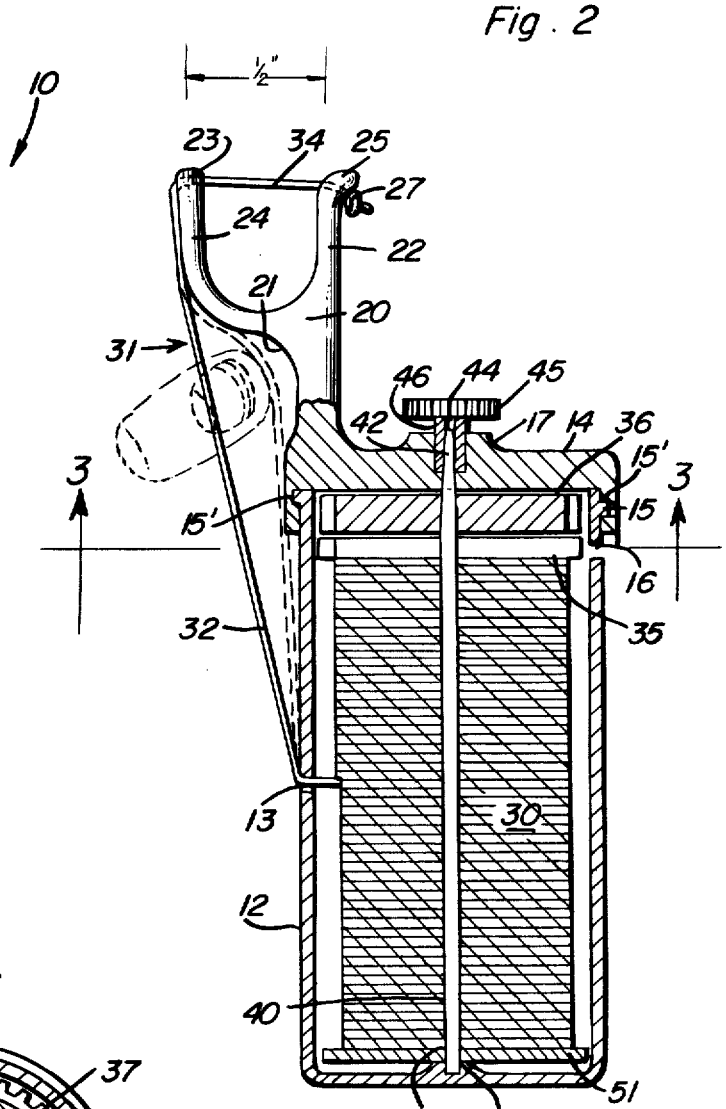
FIG. 2 is an enlarged side elevational view, partly in cross-section, of FIG. 1.
Figure 4:
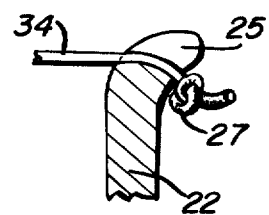
FIG. 4 is a greatly enlarged view, of the end tip part, partly in cross-section, showing the dental floss and knot retaining structure of FIGS. 1 and 2.

In normal use a spool of dental floss 30 will be mounted within the container receptacle with a free end 32 extending therefrom with said end passing over the member 24, as best seen in FIGS. 1 and 2, through the notch 23, and with an appropriate knot 27 tied at the end thereof, placed releasably into the notch 25. FIG. 4 best depicts this retention structure in enlarged detail.

As can be readily visualized by looking at FIG. 2, a user will hold the entire device in one hand and with the index finger of said hand apply appropriate tension to the dental floss portion 31 stretched across the outer portion of tine 24 and the outer portion of the main support 20, as shown in dotted lines in FIG. 2. By this means, the right degree of tension may be maintained on the stretched portion of dental floss 34 between the notches 23 and 25.

Looking now at FIG. 2, the rewind and main tension means for the spool 30 will be described. The lower end of the receptacle has an upstanding bearing projection 38 with a central aperture therein for receiving a center pin 40 for rotatably mounting and supporting the dental floss spool 30. An end flange 51 with aperture 33 therein is provided at this lower end of the dental floss spool. On the upper end of the spool, a tooth or serrated flange 35 is provided. This flange rests against the top outer layer of dental floss and provides a means for rewinding the dental floss spool. A slot 16 is provided along the upper edge of the receptacle 12 for the purpose of engaging the teeth on the spool flange 35. One slot is shown, but several slots may be provided in the receptacle 12, if desired. However, only one slot normally is necessary.

Figure 3:
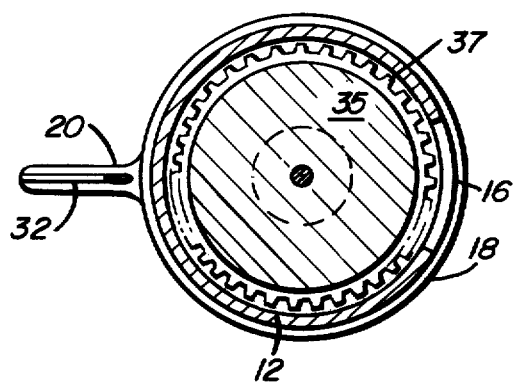
FIG. 3 is a plan view taken generally along the line 3—3 of FIG. 2.

FIG. 3 shows the opening or slot 16 as in alignment with the teeth 37 on the spool flange 35.

In order to apply a light amount of friction between the top portion of the toothed flange 35 and the inner side of the cover cap 14, a portion of sponge rubber 36 or the like is provided. The spool spindle 40 has a tapered end 42 which is receivable in the center aperture of hub 46 of the locking knob 44. The locking knob 44 has teeth or serrations 45 thereabout to form a good positive and easy finger grip surface. As can be visualized, once a user has rotated or rewound the dental floss spool 30 the proper amount by means of the toothed flange 35 through the aperture 16, this tension and spacing may be locked by merely pressing the knob 44 firmly inwardly to wedge the tapered portion 42 and the complementary inside tapered aperture of the hub 46 tightly against one another.

As can be readily visualized from the above description and the figures of the drawing associated therewith, this new and unique device offers a convenient and easily used applicator for dispensing and holding dental floss in order to effectively clean a person's teeth and gums. The double tension structure provides a quick and easy way of extending the desired amount of usable dental floss across the spaced supports 22 and 24 and the notches contained therein, and also prevents excess floss from spilling out of the container receptacle and being wasted. If too much floss is initially dispensed, it is a quick and simple operation to rewind the excess back into the container by means of the serrated spool flange 35 and lock device by means of locking knob 44. The user then can apply whatever additional tension is needed by means of an index finger against the stretched floss across the curved recessed area 21, as best seen in FIG. 2.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A dental floss applicator comprising; a floss holding receptacle for receiving a spool of dental floss, a removable cover for the receptacle, means between the cover and the spool of floss contained within the receptacle for applying tension friction thereto, an U-shaped structure mounted on the top of the removable cover for holding a length of floss between the tips of the U-shaped structure, further means for permitting additional tension to be applied to the length of floss between the tips of the U-shaped structure as the applicator is being used for teeth cleaning purposes, the means between the cover and the spool of dental floss for applying friction thereto including a washer of resilient material between the inside of the receptacle cover and the spool of floss, the further means including a recessed outer edge of the dental floss supporting U-shaped structure which is designed for reception and engagement by a user's index finger with a portion of the floss therebetween, the U-shaped supporting structure including an upright extending member with a notch at the outer tip thereof, another extending member projecting outwardly and upwardly from the first member and parallel thereto at the outer portion thereof, the second outwardly extending member also having a notch on the outer tip thereof, the washer of resilient material being made of sponge rubber, with rewind mechanism associated with the spool of dental floss, the rewind mechanism including a flanged serrated disk at one end of the spool of dental floss, and an access slot appropriately provided in the receptacle so as to be opposite said serrated flange for access to the serrations thereon for the purpose of applying rewind movement to the spool of dental floss.

2. The structure as set forth in claim 1, wherein the cover includes at least three spiral recesses on the inside thereof for receiving corresponding complementary projecting nubs on the dental floss holding receptacle.

3. The structure as set forth in claim 2, wherein the dental floss contained within the receptacle emerges from an aperture spaced approximately in the center of the elongated floss holding receptacle.

4. A dental floss applicator comprising; a floss holding receptacle for receiving a spool of dental floss, a removable cover for the receptacle, means between the cover and the spool of floss contained within the receptacle for applying tension friction thereto, an U-shaped structure mounted on the top of the removable cover for holding a length of floss between the tips of the U-shaped structure, further means for permitting additional tension to be applied to the length of floss between the tips of the U-shaped structure as the applicator is being used for teeth cleaning purposes, the means between the cover and the spool of dental floss for retaining friction therein including a washer of resilient material between the inside of the receptacle cover and the spool of floss, the receptacle having at least three projections extending along the upper outer edge thereof and the removable cover has complementary thread-like notches along the inside edge thereof for reception of the projections in order to quickly and removably fasten the two structures together, a spool flange serrated dish member arranged for use as a dental floss spool rewind structure, and an appropriate access slot provided in the receptacle for permitting access to said serrated spool flange.

5. A dental floss applicator comprising; a floss holding receptacle for receiving a spool of dental floss, a removable cover for the receptacle, means between the cover and the spool of floss contained within the receptacle for applying tension friction thereto, an U-shaped structure mounted on the top of the removable cover for holding a length of floss between the tips of the U-shaped structure, further means for permitting additional tension to be applied to the length of floss between the tips of the U-shaped structure as the applicator is being used for teeth cleaning purposes, a spool flange serrated disk member arranged for use as a dental floss spool rewind structure, and an appropriate access slot provided in the receptacle for permitting access to said serrated spool flange.

* * * * *